(12) United States Patent
Moriyama et al.

(10) Patent No.: US 12,721,675 B2
(45) Date of Patent: Sep. 1, 2026

(54) ENERGY-EMITTING DEVICES FOR ELONGATED MEDICAL ASSEMBLY

(71) Applicant: Boston Scientific Medical Device Limited, Galway (IE)

(72) Inventors: Eduardo Moriyama, Richmond (CA); Kaylie Lau, Toronto (CA); Guiseppe Mariconda, Newmarket (CA)

(73) Assignee: Boston Scientific Medical Device Limited, Galway (IE)

( * ) Notice: Subject to any disclaimer, the term of this patent is extended or adjusted under 35 U.S.C. 154(b) by 919 days.

(21) Appl. No.: 17/996,015

(22) PCT Filed: Jun. 15, 2021

(86) PCT No.: PCT/IB2021/055273

§ 371 (c)(1),
(2) Date: Oct. 12, 2022

(87) PCT Pub. No.: WO2021/255643

PCT Pub. Date: Dec. 23, 2021

(65) Prior Publication Data

US 2023/0190330 A1 Jun. 22, 2023

Related U.S. Application Data

(60) Provisional application No. 63/040,683, filed on Jun. 18, 2020.

(51) Int. Cl.
*A61B 18/14* (2006.01)
*A61B 17/34* (2006.01)
*A61B 18/00* (2006.01)

(52) U.S. Cl.
CPC .......... *A61B 18/1492* (2013.01); *A61B 17/34* (2013.01); *A61B 17/3478* (2013.01);
(Continued)

(58) Field of Classification Search
CPC ...... A61B 18/1492; A61B 2018/00351; A61B 17/3478; A61B 2017/00243;
(Continued)

(56) References Cited

U.S. PATENT DOCUMENTS 175,254 A 3/1876 Oberly
827,626 A 7/1906 Gillet
(Continued)

FOREIGN PATENT DOCUMENTS

CN 101309651 B * 12/2011 ......... A61B 18/1492
WO WO-0009027 A1 * 2/2000 ............. A61B 18/14
(Continued)

OTHER PUBLICATIONS

CN-101309651-B, English language machine translation (Year: 2011).*

(Continued)

*Primary Examiner* — Wesley G Harris
(74) *Attorney, Agent, or Firm* — Nelson Mullins Riley & Scarborough LLP

(57) ABSTRACT

At least one energy-emitting device configured to selectively initially emit and direct energy for the initial formation of a puncture hole through a biological feature. At least one other energy-emitting device configured to further emit and direct energy for subsequent or further enlargement of the puncture hole after the initial formation of the puncture hole by said at least one energy-emitting device.

14 Claims, 7 Drawing Sheets

(52) U.S. Cl.
CPC ............... *A61B 2018/00351* (2013.01); *A61B 2018/00601* (2013.01); *A61B 2018/1425* (2013.01); *A61B 2018/1427* (2013.01); *A61B 2018/1475* (2013.01)

(58) Field of Classification Search
CPC .......... A61B 2017/00247; A61B 2018/00577; A61B 2018/00601; A61B 2018/00791; A61B 2018/1475; A61B 17/34; A61B 2018/1425; A61B 2018/1427
See application file for complete search history.

(56) References Cited

U.S. PATENT DOCUMENTS 848,711 A 4/1907 Daniel
1,072,954 A 9/1913 Junn
1,279,654 A 9/1918 Charlesworth
1,918,094 A 7/1933 Geekas
1,996,986 A 4/1935 Weinberg
2,021,989 A 11/1935 De Master
2,146,636 A 2/1939 Lipchow
3,429,574 A 2/1969 Williams
3,448,739 A 6/1969 Stark et al.
3,575,415 A 4/1971 Fulp et al.
3,595,239 A 7/1971 Petersen
4,129,129 A 12/1978 Amrine
4,244,362 A 1/1981 Anderson
4,401,124 A 8/1983 Guess et al.
4,639,252 A 1/1987 Kelly et al.
4,641,649 A 2/1987 Walinsky et al.
4,669,467 A 6/1987 Willett et al.
4,682,596 A 7/1987 Bales et al.
4,790,311 A 12/1988 Ruiz
4,790,809 A 12/1988 Kuntz
4,793,350 A 12/1988 Mar et al.
4,807,620 A 2/1989 Strul et al.
4,832,048 A 5/1989 Cohen
4,840,622 A 6/1989 Hardy
4,863,441 A 9/1989 Lindsay et al.
4,884,567 A 12/1989 Elliott et al.
4,892,104 A 1/1990 Ito et al.
4,896,671 A 1/1990 Cunningham et al.
4,928,693 A 5/1990 Goodin et al.
4,936,281 A 6/1990 Stasz
4,960,410 A 10/1990 Pinchuk
4,977,897 A 12/1990 Hurwitz
4,998,933 A 3/1991 Eggers et al.
5,006,119 A 4/1991 Acker et al.
5,019,076 A 5/1991 Yamanashi et al.
5,047,026 A 9/1991 Rydell
5,081,997 A 1/1992 Bosley et al.
5,098,431 A 3/1992 Rydell
5,112,048 A 5/1992 Kienle
5,154,724 A 10/1992 Andrews
5,201,756 A 4/1993 Horzewski et al.
5,209,741 A 5/1993 Spaeth
5,211,183 A 5/1993 Wilson
5,221,256 A 6/1993 Mahurkar
5,230,349 A 7/1993 Langberg
5,281,216 A 1/1994 Klicek
5,300,068 A 4/1994 Rosar et al.
5,300,069 A 4/1994 Hunsberger et al.
5,314,418 A 5/1994 Takano et al.
5,318,525 A 6/1994 West et al.
5,327,905 A 7/1994 Avitall
5,364,393 A 11/1994 Auth et al.
5,372,596 A 12/1994 Klicek et al.
5,380,304 A 1/1995 Parker
5,397,304 A 3/1995 Truckai
5,403,338 A 4/1995 Milo
5,423,809 A 6/1995 Klicek
5,425,382 A 6/1995 Golden et al.
5,490,859 A 2/1996 Mische et al.
5,497,774 A 3/1996 Swartz et al.
5,507,751 A 4/1996 Goode et al.
5,509,411 A 4/1996 Littmann et al.
5,540,681 A 7/1996 Strul et al.
5,545,200 A 8/1996 West et al.
5,555,618 A 9/1996 Winkler
5,571,088 A 11/1996 Lennox et al.
5,575,766 A 11/1996 Swartz et al.
5,575,772 A 11/1996 Lennox
5,599,347 A 2/1997 Hart et al.
5,605,162 A 2/1997 Mirzaee et al.
5,617,878 A 4/1997 Taheri
5,622,169 A 4/1997 Golden et al.
5,624,430 A 4/1997 Eton et al.
5,667,488 A 9/1997 Lundquist et al.
5,673,695 A 10/1997 Mcgee et al.
5,674,208 A 10/1997 Berg et al.
5,683,366 A 11/1997 Eggers et al.
5,720,744 A 2/1998 Eggleston et al.
5,741,249 A 4/1998 Moss et al.
5,766,135 A 6/1998 Terwilliger
5,779,688 A 7/1998 Imran et al.
5,810,764 A 9/1998 Eggers et al.
5,814,028 A 9/1998 Swartz et al.
5,830,214 A 11/1998 Flom et al.
5,836,875 A 11/1998 Webster, Jr.
5,849,011 A 12/1998 Jones et al.
5,851,210 A 12/1998 Torossian
5,885,227 A 3/1999 Finlayson
5,888,201 A 3/1999 Stinson et al.
5,893,848 A 4/1999 Negus et al.
5,893,885 A 4/1999 Webster, Jr.
5,904,679 A 5/1999 Clayman
5,916,210 A 6/1999 Winston
5,921,957 A 7/1999 Killion et al.
5,931,818 A 8/1999 Werp et al.
5,944,023 A 8/1999 Johnson et al.
5,951,482 A 9/1999 Winston et al.
5,957,842 A 9/1999 Littmann et al.
5,964,757 A 10/1999 Ponzi
5,967,976 A 10/1999 Larsen et al.
5,989,276 A 11/1999 Houser et al.
6,007,555 A 12/1999 Devine
6,009,877 A 1/2000 Edwards
6,013,072 A 1/2000 Winston et al.
6,017,340 A 1/2000 Cassidy et al.
6,018,676 A 1/2000 Davis et al.
6,022,362 A * 2/2000 Lee .................... A61B 10/0275 600/564
6,030,380 A 2/2000 Auth et al.
6,032,674 A 3/2000 Eggers et al.
6,048,349 A 4/2000 Winston et al.
6,053,870 A 4/2000 Fulton, III
6,053,904 A 4/2000 Scribner et al.
6,056,747 A 5/2000 Saadat et al.
6,063,093 A 5/2000 Winston et al.
6,093,185 A 7/2000 Ellis et al.
6,106,515 A 8/2000 Winston et al.
6,106,520 A 8/2000 Laufer et al.
6,117,131 A * 9/2000 Taylor ................ A61B 18/1206 606/41
6,142,992 A 11/2000 Cheng et al.
6,146,380 A 11/2000 Racz et al.
6,155,264 A 12/2000 Ressemann et al.
6,156,031 A 12/2000 Aita et al.
6,171,305 B1 * 1/2001 Sherman ............ A61B 18/1492 606/41
6,179,824 B1 1/2001 Eggers et al.
6,193,676 B1 2/2001 Winston et al.
6,193,715 B1 2/2001 Wrublewski et al.
6,210,408 B1 4/2001 Chandrasekaran et al.
6,217,575 B1 4/2001 Devore et al.
6,221,061 B1 4/2001 Engelson et al.
6,228,076 B1 5/2001 Winston et al.
6,245,054 B1 6/2001 Fuimaono et al.
6,267,758 B1 7/2001 Daw et al.
6,283,983 B1 9/2001 Makower et al.
6,292,678 B1 9/2001 Hall et al.
6,293,945 B1 9/2001 Parins et al.
6,296,615 B1 10/2001 Brockway et al.

(56) References Cited

U.S. PATENT DOCUMENTS 6,296,636 B1 10/2001 Cheng et al.
6,302,898 B1 10/2001 Edwards et al.
6,304,769 B1 10/2001 Arenson et al.
6,315,777 B1 11/2001 Comben
6,328,699 B1 12/2001 Eigler et al.
6,331,166 B1 * 12/2001 Burbank ................ A61B 90/17 606/45
6,360,128 B2 3/2002 Kordis et al.
6,364,877 B1 4/2002 Goble et al.
6,385,472 B1 5/2002 Hall et al.
6,394,976 B1 5/2002 Winston et al.
6,395,002 B1 5/2002 Ellman et al.
6,419,674 B1 7/2002 Bowser et al.
6,428,551 B1 8/2002 Hall et al.
6,450,989 B2 9/2002 Dubrul et al.
6,475,214 B1 11/2002 Moaddeb
6,485,485 B1 11/2002 Winston et al.
6,508,754 B1 1/2003 Liprie et al.
6,524,303 B1 2/2003 Garibaldi
6,530,923 B1 3/2003 Dubrul et al.
6,554,827 B2 4/2003 Chandrasekaran et al.
6,562,031 B2 5/2003 Chandrasekaran et al.
6,562,049 B1 5/2003 Norlander et al.
6,565,562 B1 5/2003 Shah et al.
6,607,529 B1 8/2003 Jones et al.
6,632,222 B1 10/2003 Edwards et al.
6,639,999 B1 10/2003 Cookingham et al.
6,650,923 B1 11/2003 Lesh et al.
6,651,672 B2 11/2003 Roth
6,662,034 B2 12/2003 Segner et al.
6,663,621 B1 12/2003 Winston et al.
6,702,811 B2 3/2004 Stewart et al.
6,709,444 B1 3/2004 Makower
6,723,052 B2 4/2004 Mills
6,733,511 B2 5/2004 Hall et al.
6,740,103 B2 5/2004 Hall et al.
6,752,800 B1 6/2004 Winston et al.
6,755,816 B2 6/2004 Ritter et al.
6,811,544 B2 11/2004 Schaer
6,814,733 B2 11/2004 Schwartz et al.
6,820,614 B2 11/2004 Bonutti
6,834,201 B2 12/2004 Gillies et al.
6,842,639 B1 1/2005 Winston et al.
6,852,109 B2 2/2005 Winston et al.
6,855,143 B2 2/2005 Davison et al.
6,860,856 B2 3/2005 Ward et al.
6,869,431 B2 3/2005 Maguire et al.
6,911,026 B1 6/2005 Hall et al.
6,951,554 B2 10/2005 Johansen et al.
6,951,555 B1 10/2005 Suresh et al.
6,955,675 B2 10/2005 Jain
6,970,732 B2 11/2005 Winston et al.
6,980,843 B2 12/2005 Eng et al.
7,029,470 B2 4/2006 Francischelli et al.
7,056,294 B2 6/2006 Khairkhahan et al.
7,083,566 B2 8/2006 Tornes et al.
7,112,197 B2 9/2006 Hartley et al.
7,335,197 B2 2/2008 Sage et al.
7,618,430 B2 11/2009 Scheib
7,651,492 B2 1/2010 Wham
7,666,203 B2 2/2010 Chanduszko et al.
7,678,081 B2 3/2010 Whiting et al.
7,682,360 B2 3/2010 Guerra
7,828,796 B2 11/2010 Wong et al.
7,900,928 B2 3/2011 Held et al.
8,192,425 B2 6/2012 Mirza et al.
8,257,323 B2 9/2012 Joseph et al.
8,388,549 B2 3/2013 Paul et al.
8,500,697 B2 8/2013 Kurth et al.
11,339,579 B1 5/2022 Stearns
2001/0012934 A1 8/2001 Chandrasekaran et al.
2001/0021867 A1 9/2001 Kordis et al.
2002/0019644 A1 2/2002 Hastings et al.
2002/0022781 A1 2/2002 McIntire et al.
2002/0022836 A1 2/2002 Goble et al.
2002/0035361 A1 3/2002 Houser et al.
2002/0087153 A1 7/2002 Roschak et al.
2002/0087156 A1 7/2002 Maguire et al.
2002/0111618 A1 8/2002 Stewart et al.
2002/0123749 A1 * 9/2002 Jain .................... A61B 18/1492 606/41
2002/0147485 A1 10/2002 Mamo et al.
2002/0169377 A1 11/2002 Khairkhahan et al.
2002/0188302 A1 12/2002 Berg et al.
2002/0198521 A1 12/2002 Maguire
2003/0032929 A1 2/2003 Mcguckin
2003/0040742 A1 2/2003 Underwood et al.
2003/0144658 A1 7/2003 Schwartz et al.
2003/0158480 A1 8/2003 Tornes et al.
2003/0163153 A1 8/2003 Scheib
2003/0220640 A1 * 11/2003 Lee ..................... A61B 18/148 606/45
2003/0225392 A1 12/2003 Mcmichael et al.
2004/0015162 A1 1/2004 Mcgaffigan
2004/0024396 A1 2/2004 Eggers
2004/0030328 A1 2/2004 Eggers et al.
2004/0044350 A1 3/2004 Martin et al.
2004/0073243 A1 4/2004 Sepetka et al.
2004/0077948 A1 4/2004 Violante et al.
2004/0116851 A1 6/2004 Johansen et al.
2004/0127963 A1 7/2004 Uchida et al.
2004/0133113 A1 7/2004 Krishnan
2004/0133130 A1 7/2004 Ferry et al.
2004/0143256 A1 7/2004 Bednarek
2004/0147950 A1 7/2004 Mueller et al.
2004/0181213 A1 9/2004 Gondo
2004/0230188 A1 11/2004 Cioanta et al.
2005/0004585 A1 1/2005 Hall et al.
2005/0010208 A1 1/2005 Winston et al.
2005/0049628 A1 3/2005 Schweikert et al.
2005/0059966 A1 3/2005 Mcclurken et al.
2005/0065507 A1 3/2005 Hartley et al.
2005/0085806 A1 4/2005 Auge et al.
2005/0096529 A1 5/2005 Cooper et al.
2005/0101984 A1 5/2005 Chanduszko et al.
2005/0119556 A1 6/2005 Gillies et al.
2005/0137527 A1 6/2005 Kunin
2005/0149012 A1 7/2005 Penny et al.
2005/0203504 A1 9/2005 Wham et al.
2005/0203507 A1 9/2005 Truckai et al.
2005/0261607 A1 11/2005 Johansen et al.
2005/0288631 A1 12/2005 Lewis et al.
2006/0041253 A1 2/2006 Newton et al.
2006/0074398 A1 4/2006 Whiting et al.
2006/0079769 A1 4/2006 Whiting et al.
2006/0079787 A1 4/2006 Whiting et al.
2006/0079884 A1 4/2006 Manzo et al.
2006/0085054 A1 4/2006 Zikorus et al.
2006/0089638 A1 4/2006 Carmel et al.
2006/0106375 A1 5/2006 Werneth et al.
2006/0135962 A1 6/2006 Kick et al.
2006/0142756 A1 6/2006 Davies et al.
2006/0189972 A1 8/2006 Grossman
2006/0241586 A1 10/2006 Wilk
2006/0247672 A1 11/2006 Mdlund et al.
2006/0264927 A1 11/2006 Ryan
2006/0276710 A1 12/2006 Krishnan
2007/0060879 A1 3/2007 Weitzner et al.
2007/0066975 A1 3/2007 Wong et al.
2007/0118099 A1 5/2007 Trout
2007/0123964 A1 5/2007 Davies et al.
2007/0167775 A1 7/2007 Kochavi et al.
2007/0208256 A1 9/2007 Marilla
2007/0225681 A1 9/2007 House
2007/0270791 A1 11/2007 Wang et al.
2008/0039865 A1 2/2008 Shaher et al.
2008/0042360 A1 2/2008 Veikley
2008/0086120 A1 4/2008 Mirza et al.
2008/0097213 A1 4/2008 Carlson et al.
2008/0108987 A1 5/2008 Bruszewski et al.
2008/0146918 A1 6/2008 Magnin et al.
2008/0171934 A1 7/2008 Greenan et al.
2008/0208121 A1 8/2008 Youssef et al.
2008/0275439 A1 11/2008 Francischelli et al.

(56) References Cited

U.S. PATENT DOCUMENTS

2009/0105742 A1 4/2009 Kurth et al.
2009/0138009 A1 5/2009 Mswanathan et al.
2009/0163850 A1 6/2009 Betts et al.
2009/0177114 A1 7/2009 Chin et al.
2009/0264977 A1 10/2009 Bruszewski et al.
2010/0087789 A1 4/2010 Leeflang et al.
2010/0125282 A1 5/2010 Machek et al.
2010/0168684 A1 7/2010 Ryan
2010/0179632 A1 7/2010 Bruszewski et al.
2010/0191142 A1* 7/2010 Paul ..................... A61B 5/6852 600/549
2010/0194047 A1 8/2010 Sauerwine
2011/0046619 A1 2/2011 Ducharme
2011/0152716 A1 6/2011 Chudzik et al.
2011/0160592 A1 6/2011 Mitchell
2011/0190763 A1 8/2011 Urban et al.
2012/0232546 A1 9/2012 Mirza et al.
2012/0265055 A1 10/2012 Melsheimer et al.
2012/0330156 A1 12/2012 Brown et al.
2013/0046305 A1* 2/2013 Davies ............... A61B 18/1492 606/45
2013/0184551 A1 7/2013 Paganelli et al.
2013/0184735 A1 7/2013 Fischell et al.
2013/0282084 A1 10/2013 Mathur et al.
2014/0206987 A1 7/2014 Urbanski et al.
2014/0296769 A1 10/2014 Hyde et al.
2016/0220741 A1 8/2016 Garrison et al.
2018/0140289 A1 5/2018 Benning et al.
2019/0021763 A1 1/2019 Zhou et al.
2019/0247035 A1 8/2019 Gittard et al.
2020/0060710 A1 2/2020 Urbanski et al.

FOREIGN PATENT DOCUMENTS

WO WO-0182998 A2 * 11/2001 ......... A61B 10/0266
WO 2019/181611 A1 9/2019
WO 2019/188916 A1 10/2019

OTHER PUBLICATIONS

International Search Report and Written Opinion received for PCT Patent Application No. PCT/IB2021/055273, mailed on Sep. 16, 2021, 9 pages.

* cited by examiner

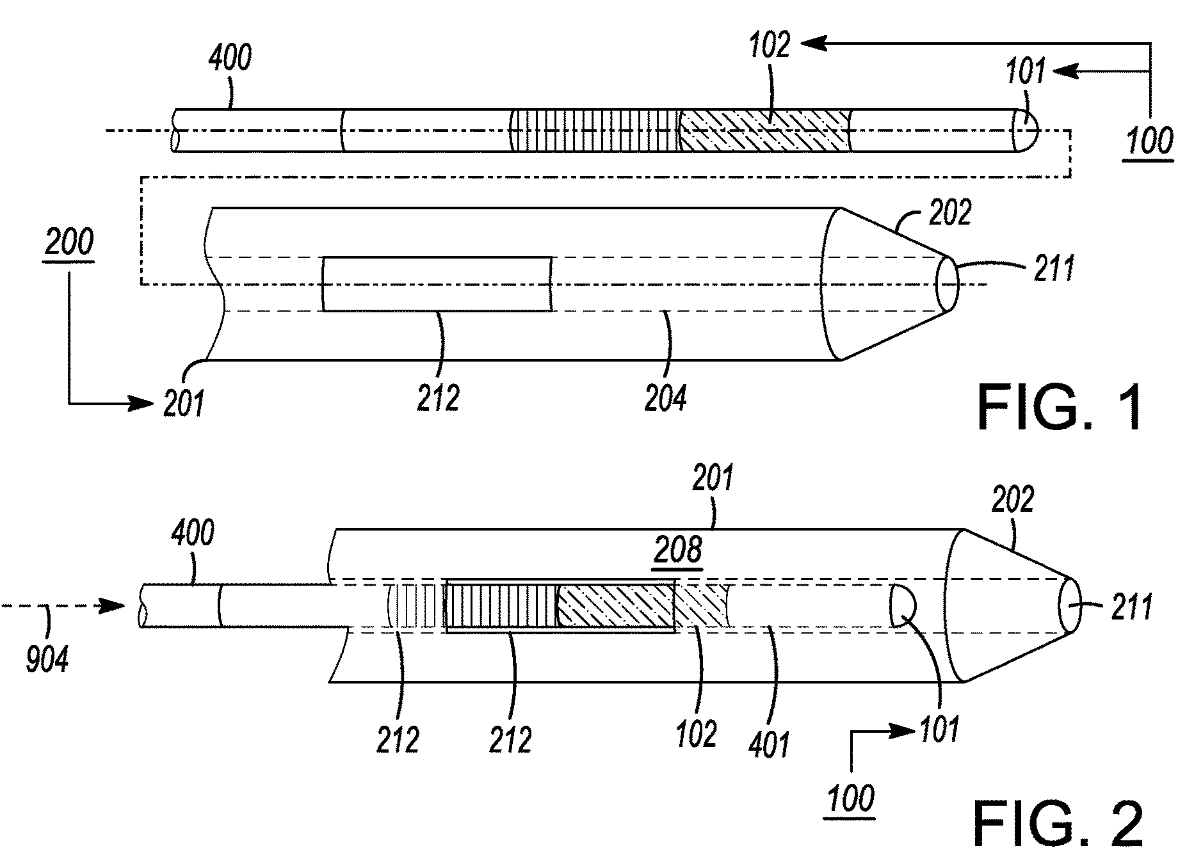
FIG. 1
FIG. 2
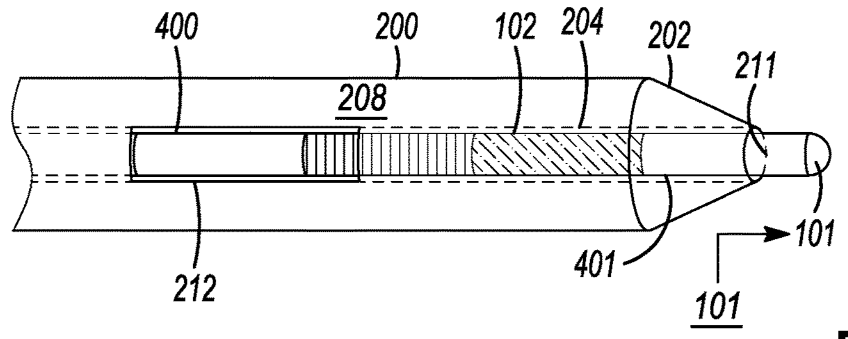
FIG. 3
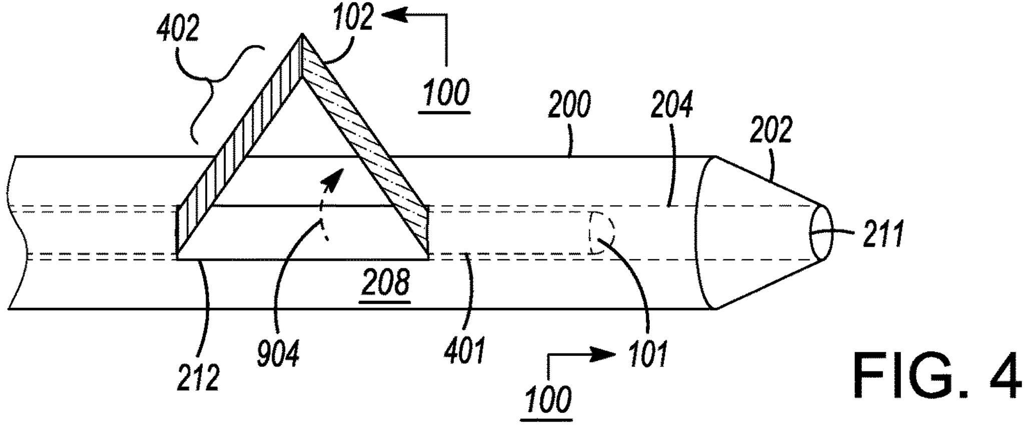
FIG. 4

100
400
412
411
102
401
101

101
201
200
204
102
900
100
208
211
400
904
401
202

200
201
204
102
401
900
100
101
400
902
904
202
211

200
900
100
201
204
102
101
400
401
902
904
202

ENERGY-EMITTING DEVICES FOR ELONGATED MEDICAL ASSEMBLY

TECHNICAL FIELD

This document relates to the technical field of (and is not limited to) (A) energy-emitting devices for use with an elongated medical assembly (and method therefor), and/or (B) an elongated medical assembly including energy-emitting devices (and method therefor).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with the existing (known) energy-emitting devices (also called the existing technology). After much study of, and experimentation with, the existing (known) energy-emitting devices, an understanding (at least in part) of the problem and its solution have been identified (at least in part) and are articulated (at least in part) as follows:

Various procedures may require the formation of a relatively large bore hole through the inter-atrial septum of the heart (an example of a biological feature). For example, it may be necessary to deliver a relatively larger medical device from the right side to the left side of the heart of the patient. Cryoablations, mitral valve repairs and/or left atrial appendage closures are some of the procedures that may require relatively larger medical devices to access the left atrium of the heart. There are known medical devices (such as the known transseptal dilator) configured for large access. The known procedural workflow, however, may require the use of an energy-emitting needle to form a puncture hole through the septum (of the heart), and prior to using (deploying) the larger medical device, predilation of the puncture hole may be required (by using a dilation device). Utilization of these many medical devices may lead to extended surgical time and/or exposure to unwanted surgical mishaps as a result of the insertion, movement and/or removal of these medical devices (into, and out from, the patient).

In view of the foregoing problems, it may be desirable to reduce the number of medical devices required for the initial formation of the puncture hole and subsequent enlargement of the puncture hole. It may be desirable to provide an apparatus configured to selectively emit (and direct) energy (such as radio-frequency energy) to (A) initially form a puncture hole through a biological feature (such as the inter-atrial septum) of a patient, and (B) further enlarge the puncture hole (after its initial formation). It may be desirable to provide these functions and/or structures in a single apparatus, in which the apparatus is configured to (A) initially form the puncture hole (through the biological feature), and (B) subsequently dilate the puncture hole. This arrangement may streamline, at least in part, the workflow and/or reduce the number of devices in the sterile field used in a procedure, etc.

It may be desirable to create a large bore hole in the inter-atrial septum by using the apparatus. It may be desirable to provide the apparatus for creating large bore holes in other biological structures including, and not limited to, the inter-ventricular septum and blood vessels, etc.

To mitigate, at least in part, at least one problem associated with the existing technology, there is provided (in accordance with a major aspect) an apparatus. The apparatus includes and is not limited to (comprises) at least one energy-emitting device configured to selectively initially emit and direct energy for the initial formation of a puncture hole through a biological feature. At least one other energy-emitting device is configured to further selectively emit and direct energy for subsequent or further enlargement of the puncture hole after the initial formation of the puncture hole by at least one energy-emitting device. Preferably, at least one energy-emitting device and at least one other energy-emitting device are configured to be mounted proximate to a distal portion of an elongated medical needle. Even more preferably, at least one energy-emitting device, at least one other energy-emitting device and the elongated medical needle are configured to be deployed along an elongated medical assembly.

To mitigate, at least in part, at least one problem associated with the existing technology, there is provided (in accordance with a major aspect) an apparatus. The apparatus is for the formation of (is configured to form) a puncture hole to be extended through (extending through) a biological feature. The apparatus is for use with (configured to be used with or on) an elongated medical assembly. The apparatus includes and is not limited to (comprises) an energy-emitting assembly movable along the elongated medical assembly toward a position proximate to the biological feature.

The energy-emitting assembly is configured to direct, at least in part, the initial emission of energy toward, at least in part, the biological feature for the initial formation of the puncture hole, extending through the biological feature, after the energy-emitting assembly, in use, is moved along the elongated medical assembly and is positioned proximate to the biological feature.

The energy-emitting assembly is also configured to further direct, at least in part, subsequent emission of energy toward, at least in part, the biological feature neighboring (surrounding) the puncture hole for subsequent or further enlargement of the puncture hole after the energy-emitting assembly is further moved along the elongated medical assembly toward the biological feature neighboring (surrounding) the puncture hole.

To mitigate, at least in part, at least one problem associated with the existing technology, there is provided (in accordance with a major aspect) a method. The method is for the formation of a puncture hole through a biological feature by at least one energy-emitting device and at least one other energy-emitting device configured to be mounted proximate to a distal needle tip section of an elongated medical needle. The elongated medical needle is configured to be deployed along an elongated medical assembly. The method includes and is not limited to (comprises) moving a distal tip section of the elongated medical assembly to the biological feature. The method also includes moving at least one energy-emitting device and at least one other energy-emitting device by moving the distal needle tip section of the elongated medical needle along the elongated medical assembly to the biological feature. The method also includes selectively initially emitting and directing energy, via at least one energy-emitting device, for the initial formation of the puncture hole through the biological feature. The method also includes further selectively emitting and directing energy, via at least one other energy-emitting device, for subsequent or further enlargement of the puncture hole after the initial formation of the puncture hole by at least one energy-emitting device.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which:

FIG. 1 to FIG. 4 depict side perspective views of embodiments of an energy-emitting assembly including a first energy-emitting device and a second energy-emitting device.

Figure 5:
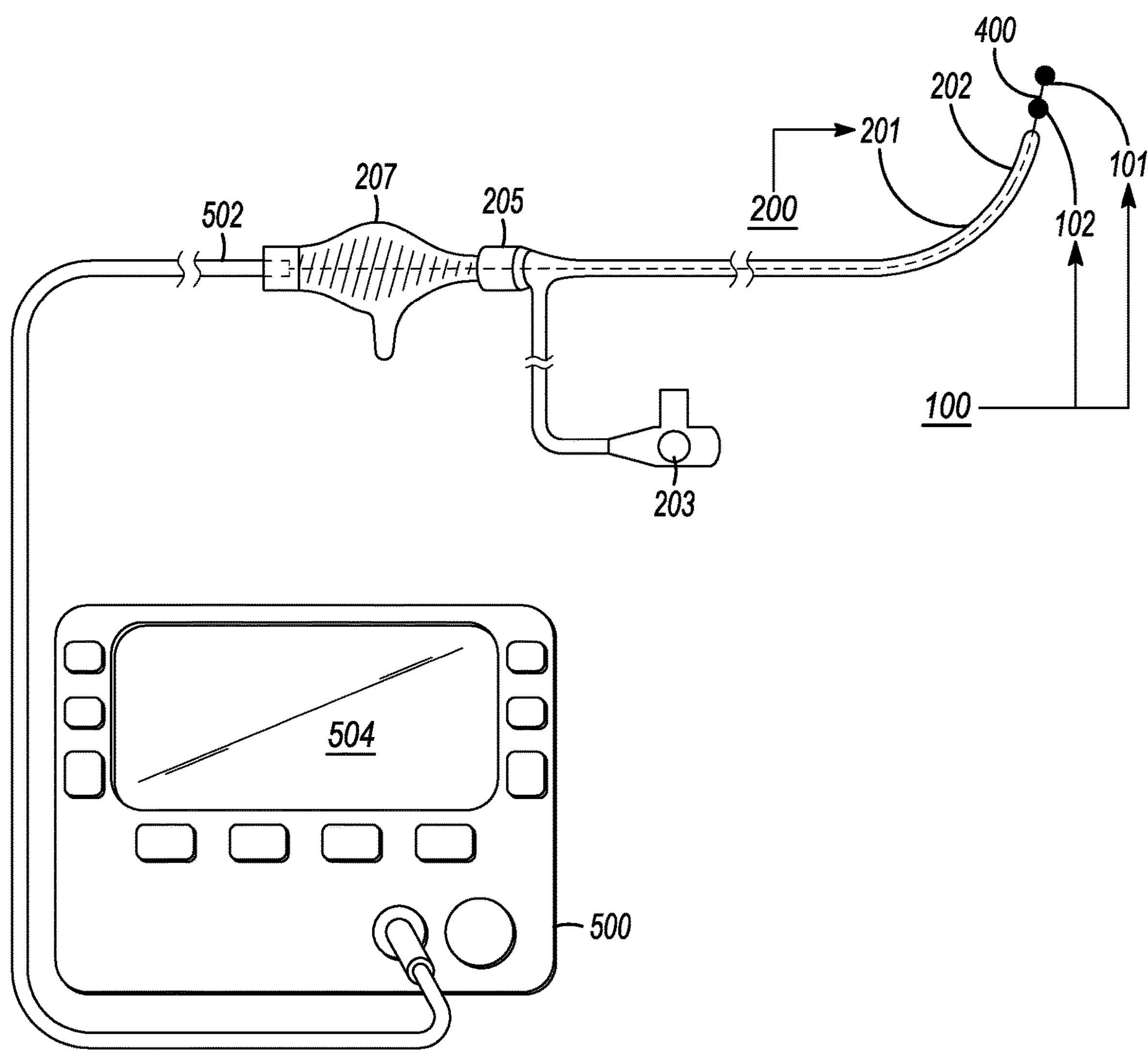
FIG. 5 depicts a side view of an embodiment of the energy-emitting assembly of FIG. 1.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS energy-emitting assembly 100
first energy-emitting device 101
one energy-emitting device 101
elongated medical assembly 200
elongated catheter assembly 201
distal tip section 202
three-way stopcock 203
lumen 204
hemostatic valve 205
handle assembly 207
side wall section 208
first portal 211
second portal 212
medical needle 400
distal needle tip section 401
triangle-shaped arrangement 402
first wire 411
second wire 412
energy source 500
connector cable 502
display device 504
guidewire assembly 600
biological feature 900
puncture hole 902
movement direction 904
distal angle 906

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

FIG. 1 to FIG. 15 are directed to a major embodiment, and FIG. 16 to FIG. 19 are directed to another major embodiment.

FIG. 1 to FIG. 4 depict side perspective views of embodiments of an energy-emitting assembly 100 including a first energy-emitting device 101 and a second energy-emitting device 102.

Referring to the embodiment as depicted in FIG. 1, the energy-emitting assembly 100 is configured to be deployed along an elongated medical assembly 200. The energy-emitting assembly 100 includes a first energy-emitting device 101 and a second energy-emitting device 102 (spaced apart from each other). Preferably, the elongated medical assembly 200 defines an elongated lumen 204 extending from a distal tip section 202 (as depicted in FIG. 1) and a proximal section (as depicted in FIG. 5). The energy-emitting assembly 100 is configured to be inserted into, and deployed along, the lumen 204 of the elongated medical assembly 200. Preferably, the elongated medical assembly 200 forms a first portal 211 and a second portal 212. The first portal 211 is configured to interact with the first energy-emitting device 101. The second portal 212 is configured to interact with the second energy-emitting device 102. It will be appreciated that in accordance with the embodiments as depicted in FIG. 16 to FIG. 19, the second portal 212 is not provided with the elongated medical assembly 200. The elongated medical assembly 200 may include (for example), a catheter assembly 201, a dilator assembly, etc., and any equivalent thereof.

Referring to the embodiment as depicted in FIG. 1, the energy-emitting assembly 100 is (preferably) configured to be mounted to an elongated medical needle 400. The elongated medical needle 400 is configured to be inserted into, and deployed along, the lumen 204 of the elongated medical assembly 200. The elongated medical needle 400 is configured to be inserted into a confined space defined by a living body (the patient). The elongated medical needle 400 includes (preferably) a relatively thin and flexible wire (an elongated flexible shaft) configured to be inserted into a confined or tortuous space (a confined space) defined by the patient. The elongated medical needle 400 is (preferably) impermeable by a bodily fluid of the patient.

Referring to the embodiment as depicted in FIG. 1, the elongated medical needle 400 and the energy-emitting assembly 100 may include (and are not limited to) a radio frequency puncture device configured to emit energy therefrom, such as the BAYLIS (TRADEMARK) POWERWIRE (REGISTERED TRADEMARK) radio frequency guidewire, manufactured by the BAYLIS MEDICAL COMPANY (headquartered in Canada).

Referring to the embodiment as depicted in FIG. 2, the elongated medical needle 400 is slidably inserted into (received by) the lumen 204 of the elongated medical assembly 200; this is done in such a way that the first energy-emitting device 101 is positionable proximate to the distal tip section 202 of the elongated medical assembly 200. The elongated medical needle 400 includes (preferably) the first energy-emitting device 101 configured to form an initial puncture through a biological wall (not depicted). The first energy-emitting device 101 is movable from within the distal tip section 202 of the elongated medical assembly 200 and out from the first portal 211. The elongated medical needle 400 includes (preferably) the second energy-emitting device 102 configured to further enlarge the puncture that was initially formed by the first energy-emitting device 101 (once the second energy-emitting device 102 is deployed, or positioned, as depicted in FIG. 4). The second energy-emitting device 102 is movable from within the lumen 204 of the distal tip section 202 and out from the second portal 212. The first energy-emitting device 101 is configured to be positioned (by movement of the elongated medical needle 400 along the elongated medical assembly 200) proximate to (or at) the catheter assembly 201 of the elongated medical assembly 200. The second energy-emitting device 102 is configured to be positioned (by movement of the elongated medical needle 400 along the elongated medical assembly 200) proximate to the second portal 212 of the elongated medical assembly 200. The first energy-emitting device 101 is configured to puncture (by forming the puncture hole 902 through) the biological feature 900 (such as a biological wall, tissue, etc.) of the patient (such as, the inter-atrial septum, etc.) while the first energy-emitting device 101 is moved out from the first portal 211 of the elongated medical assembly 200. The second energy-emitting device 102 is configured to further enlarge the puncture hole 902 (after the puncture hole 902 was initially formed by the first energy-emitting device 101) while the second energy-emitting device 102 is moved out from the second portal 212 of the elongated medical assembly 200 and while the elongated medical assembly 200 is further moved toward the puncture hole (so that the second energy-emitting device 102 may be moved toward the puncture hole).

Referring to the embodiment as depicted in FIG. 2, the elongated medical needle 400 is configured to extend toward the distal tip section 202 of the elongated medical assembly 200 (once the elongated medical needle 400 is inserted into the lumen 204 of the elongated medical assembly 200). As depicted in FIG. 2, the first energy-emitting device 101 is positioned proximate to (or at) the distal tip section 202 (near the first portal 211) of the elongated medical needle 400. The second energy-emitting device 102 is positioned proximate to the distal tip section 202 (near the second portal 212) of the elongated medical needle 400. The energy-emitting devices (101, 102) are configured to be selectively activated to emit energy (to emit energy or to deliver an amount of radio frequency energy) to a biological feature after the energy-emitting devices (101, 102) are positioned proximate to the biological feature. The surgeon (physician) may selectively control (or select) activation of the energy-emitting devices (101, 102) by using suitable equipment, such as depicted in FIG. 5, etc., and any equivalent thereof.

Referring to the embodiments as depicted in FIG. 3 and FIG. 4, the second energy-emitting device 102 is mounted to the elongated medical needle 400, and the elongated medical needle 400 is configured to selectively move (pivot) the second energy-emitting device 102 from within an interior of the elongated medical assembly 200 (as depicted in FIG. 3) to an exterior of the elongated medical assembly 200 (as depicted in FIG. 4), in which case the elongated medical needle 400 includes a memory alloy, etc., and any equivalent thereof. The second energy-emitting device 102 is configured to be moved to a position located outside of the elongated medical assembly 200; this is done in such a way that the second energy-emitting device 102 is extended, at least in part, through the second portal 212. As depicted in FIG. 4, a section of the elongated medical needle 400 surrounding the second energy-emitting device 102 is configured to form a triangle-shaped arrangement 402, etc., once (after) the section of the elongated medical needle 400 is deployed or moved out from an interior of the elongated medical assembly 200.

Referring to the embodiments as depicted in FIG. 1 to FIG. 4, the elongated medical assembly 200 forms the first portal 211 and the second portal 212 (spaced apart from each other). The first portal 211 is configured to interact with the first energy-emitting device 101. The first energy-emitting device 101 is configured to pass through (at least in part) the first portal 211. The second portal 212 is configured to interact with the second energy-emitting device 102. The second energy-emitting device 102 is configured to pass through (at least in part) the second portal 212. The elongated medical assembly 200 includes the distal tip section 202, and the distal tip section 202 forms the first portal 211.

The elongated medical assembly 200 includes a side wall section 208, and the side wall section 208 forms the second portal 212. The elongated medical needle 400 is configured to be selectively moved so that the first energy-emitting device 101 is moved from within the elongated medical assembly 200 to externally of the elongated medical assembly 200 via the first portal 211 (and may be selectively activated by the user as needed, etc.). The elongated medical needle 400 is configured to be selectively shaped or formed to move the second energy-emitting device 102 from within the elongated medical assembly 200 to externally of the elongated medical assembly 200 via the second portal 212. The second energy-emitting device 102 is configured to be moved from within the elongated medical assembly 200 and positioned outside of the elongated medical assembly 200 (by the user), and then to be selectively activated (by the user) as needed, etc. When the second energy-emitting device 102 is positioned (outside of the elongated medical assembly 200), the second energy-emitting device 102 may be selectively activated. The second energy-emitting device 102 is moved (extended) through the second portal 212 of the side wall section 208. After (or once) the energy-emitting device 102 is positioned outside of the elongated medical assembly 200, the energy-emitting device 102 (and/or a portion of the elongated medical needle 400) forms the triangle-shaped arrangement 402.

Referring to the embodiments as depicted in FIG. 1 to FIG. 4, the elongated medical assembly 200 may have various outer diameters, lengths and/or curves. The elongated medical assembly 200 may be made of a high-density polyethylene (HDPE) core, braiding pattern or formation, and/or a low-density polyethylene (LDPE) outer layer. The elongated medical assembly 200 has a tapered tip, similar to a dilator, and should have a slit located at the distal end. The elongated medical assembly 200 may include a steer mechanism (known and not depicted) positioned (preferably) in and along components of the elongated medical assembly 200 (such as, in between a high-density polyethylene (HDPE) core and a braiding formation. The steer mechanism is configured to steer or control movement of the elongated medical needle 400, etc., as required during the procedure. The elongated medical assembly 200 may be configured to be radiopaque (e.g. have a platinum/iridium band, etc.) and/or echogenic, etc., and any equivalent thereof.

Referring to the embodiments as depicted in FIG. 1 to FIG. 4, the elongated medical assembly 200 may be adapted to include a steerable catheter, etc., and any equivalent thereof. The elongated medical assembly 200 may be made of a medical grade thermoplastic elastomer material (such as the PEBAX (TRADEMARK) material manufactured by the ARKEMA Company). The elongated medical assembly 200 may be made of Nylon 12; Nylon is a generic designation for a family of synthetic polymers, based on aliphatic or semi-aromatic polyamides. Nylon is a thermoplastic silky material that can be melt-processed into fibers, films, or shapes. It is made of repeating units linked by amide links similar to the peptide bonds in proteins.

Referring to the embodiments as depicted in FIG. 1 to FIG. 4, the elongated medical assembly 200 may have side lumens, pull rings and/or pull wires (known and not depicted), etc. The elongated medical assembly 200 may have small, medium or large curves, etc. The elongated medical assembly 200 may be bi-directional, with either symmetrical or asymmetrical curves, or unidirectional, etc. Movement of the elongated medical assembly 200 may be controlled via a handle.

Referring to the embodiments as depicted in FIG. 1 to FIG. 4, the elongated medical needle 400 may have various outer diameters, such as about 0.035 inches, and/or an elongated length of about 180 centimeters. The elongated medical needle 400 may have a lever that is located distally to the second electrode and may have a pivot on each end. The elongated medical needle 400 may have a steer mechanism (known and not depicted), etc. The elongated medical needle 400 may have positional markers to confirm the position of the first energy-emitting device 101 and/or the second energy-emitting device 102. The elongated medical needle 400 is configured to form an angle between the elongated medical assembly 200 and the elongated medical needle 400 higher than 90 degrees, facilitating the cut of the tissue (reference is made to FIG. 12). The elongated medical needle 400 may be radiopaque and echogenic, etc., and any equivalent thereof.

Referring to the embodiments as depicted in FIG. 1 to FIG. 4, the elongated medical needle 400 may include a shape-memory material configured to be manipulated and/or deformed followed by a return to the original shape that the shape-memory material was set in (prior to a predetermined manipulation). Shape-memory materials (SMMs) are known and not further described in detail. Shape-memory materials are configured to recover their original shape from a significant and seemingly plastic deformation in response to a particular stimulus applied to the shape-memory material. This is known as the shape memory effect (SME). Superelasticity (in alloys) may be observed once the shape-memory material is deformed under the presence (an application) of a stimulus force.

Referring to the embodiment as depicted in FIG. 4, when the second energy-emitting device 102 is deployed (pivoted), the second energy-emitting device 102 and a portion of the elongated medical needle 400 may be extended through the second portal 212 of the elongated medical assembly 200 to form a predetermined shape (such as a triangle shape, etc.) configured to position the second energy-emitting device 102 for further enlargement of the puncture hole that was initially formed by the first energy-emitting device 101.

FIG. 5 depicts a side view of an embodiment of the energy-emitting assembly 100 of FIG. 1.

Figures 16, 17, 18, 19:
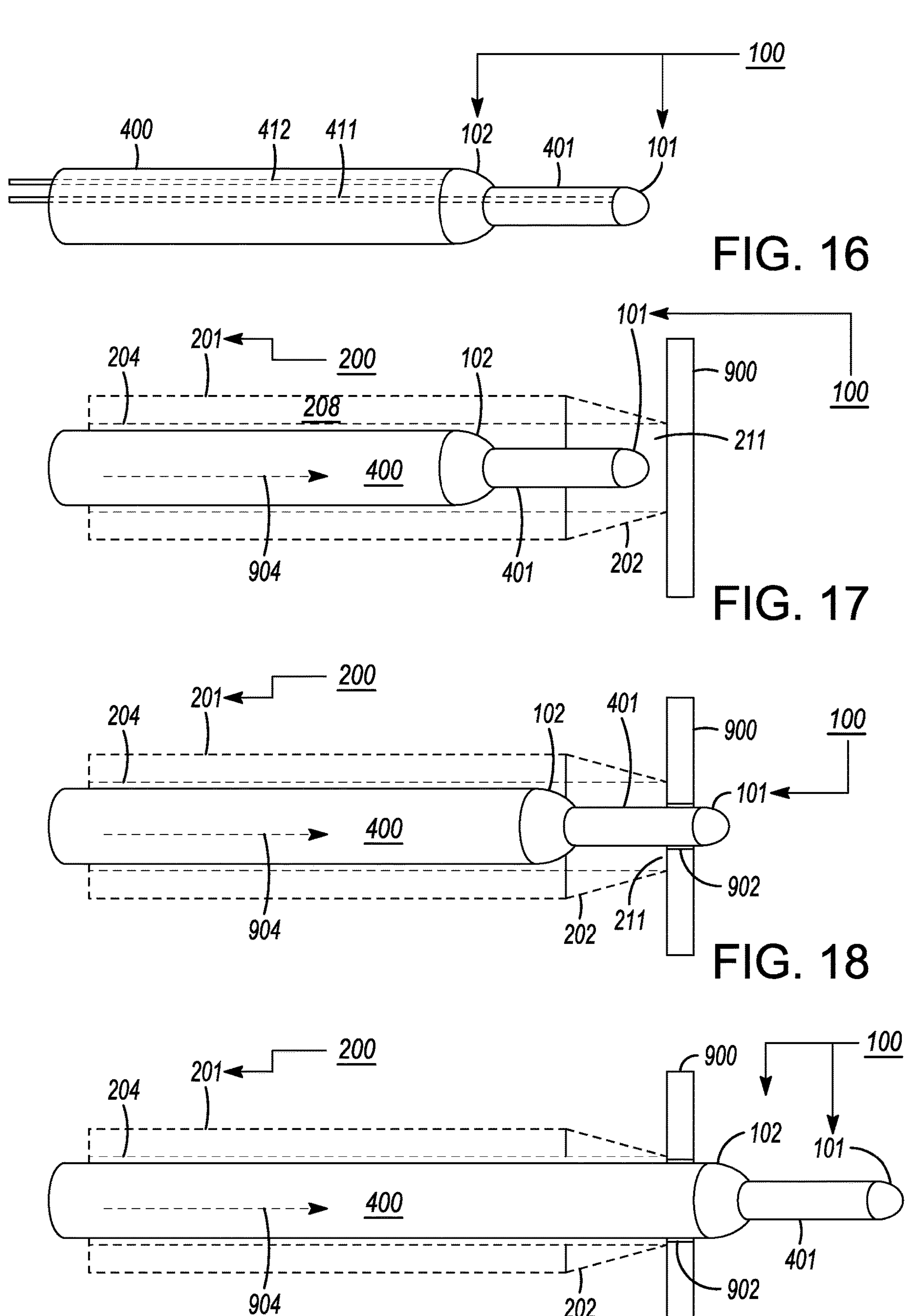
FIG. 16 to FIG. 19 depict side views of embodiments of the energy-emitting assembly of FIG. 1.

Referring to the embodiment as depicted in FIG. 5, the medical assembly 200 includes (for instance) a catheter assembly 201. The catheter assembly 201 includes, for instance, a three-way stopcock 203, a hemostatic valve 205 and a handle assembly 207, etc., and other components (known and not described in any specific details). The elongated medical needle 400 includes a first electrical wire and a second electrical wire (embodiments of which are depicted in FIG. 16). The first wire and the second wire are configured to electrically connect the first energy-emitting device 101 and the second energy-emitting device 102 (respectively) to an energy source 500 through (via) at least one connector cable 502, etc. The energy source 500 may include a radio-frequency generator, etc., and any equivalent thereof. The energy source 500 is configured to generate energy, which is conveyed to the energy-emitting devices (101, 102) via the connector cable 502 and the first and second wires of the elongated medical needle 400. The energy-emitting devices (101, 102) emit (broadcast, direct) the energy to the neighboring tissue of the patient after the energy-emitting devices (101, 102) are positioned accordingly. The energy source 500 may include a display device 504 configured to display parameters (such as voltages, etc.) associated with the first energy-emitting device 101 and/or the second energy-emitting device 102, etc. The energy-emitting devices (101, 102) may include electrodes, etc., and any equivalents thereof. The surgeon (physician) may control which of the energy-emitting devices (101, 102) is activated to deliver or emit energy (such as, radio-frequency energy, etc.), and any equivalent thereof.

Referring to the embodiment as depicted in FIG. 5, the energy-emitting assembly 100, the elongated medical assembly 200 and the elongated medical needle 400 include bio-compatible material properties suitable for sufficient performance (such as, dielectric strength, thermal performance, insulation, corrosion, water and/or heat resistance) in compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

FIG. 6 to FIG. 12 depict side views (FIG. 6 and FIG. 7) and side perspective views (FIG. 8 to FIG. 12) of embodiments of the energy-emitting assembly 100 of FIG. 1 (and a workflow manner or method for use thereof).

Figure 6:
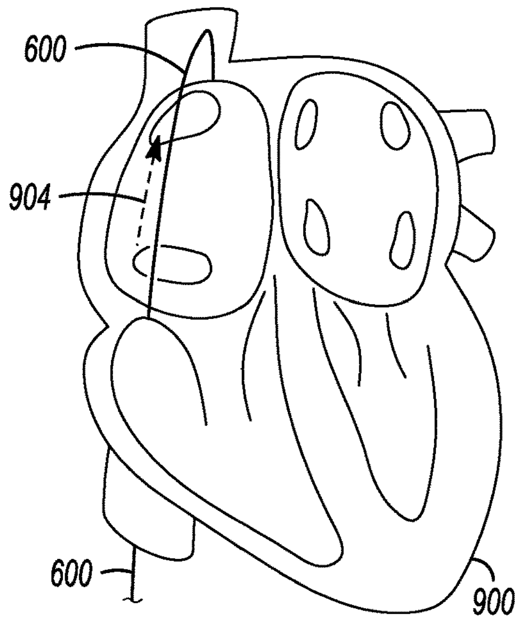
FIG. 6 to FIG. 12 depict side views (FIG. 6 and FIG. 7) and side perspective views (FIG. 8 to FIG. 12) of embodiments of the energy-emitting assembly of FIG. 1.

Referring to the embodiment as depicted in FIG. 6, the method includes the step of advancing an elongated guidewire assembly 600 toward a biological feature 900 (such as, into the superior vena cava of the heart of the patient).

Figure 7:
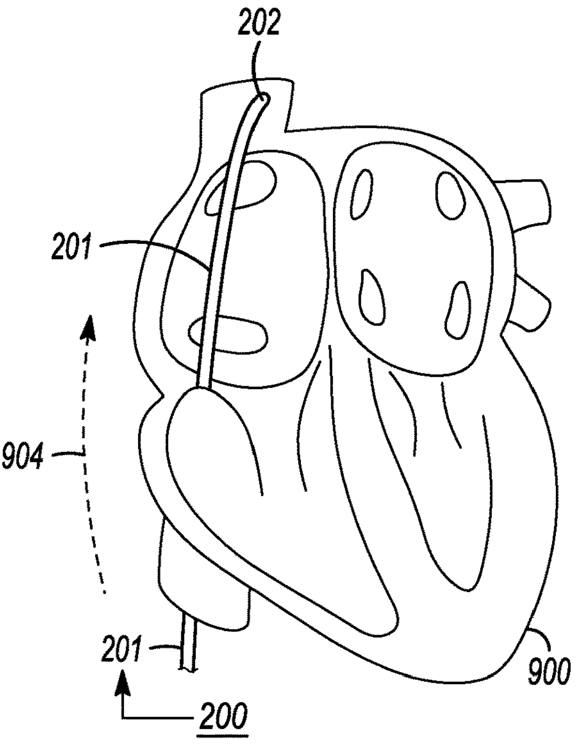

Referring to the embodiment as depicted in FIG. 7, the method further includes the step of advancing the elongated medical assembly 200 over the elongated guidewire assembly 600 into the superior vena cava. The method further includes the step of removing the elongated guidewire assembly 600 once the elongated medical assembly 200 is positioned as desired (for the purposes of the procedure).

Figure 8:
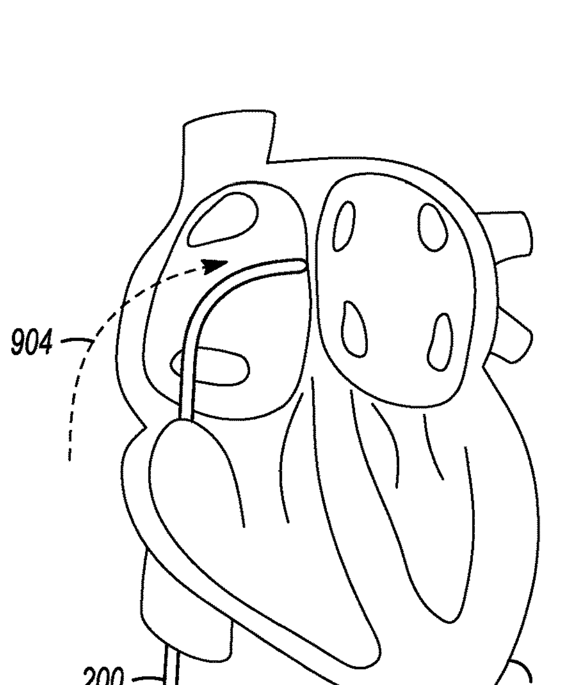

Referring to the embodiment as depicted in FIG. 8, the method further includes the step of moving and/or rotating (clocking) the elongated medical assembly 200 (such as from the 3 o'clock position to the 6 o'clock position).

Figure 9:
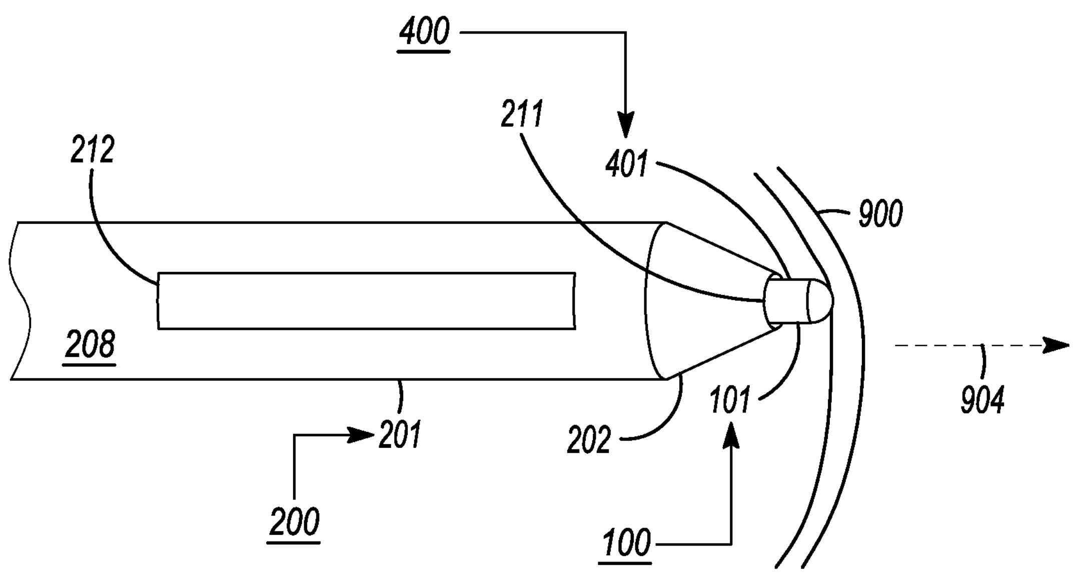

Referring to the embodiment as depicted in FIG. 9, the method further includes the step of moving the elongated medical assembly 200 (along the movement direction 904) to the biological feature 900 (such as, the fossa ovalis of the heart), and tenting the biological feature 900.

Figure 10:
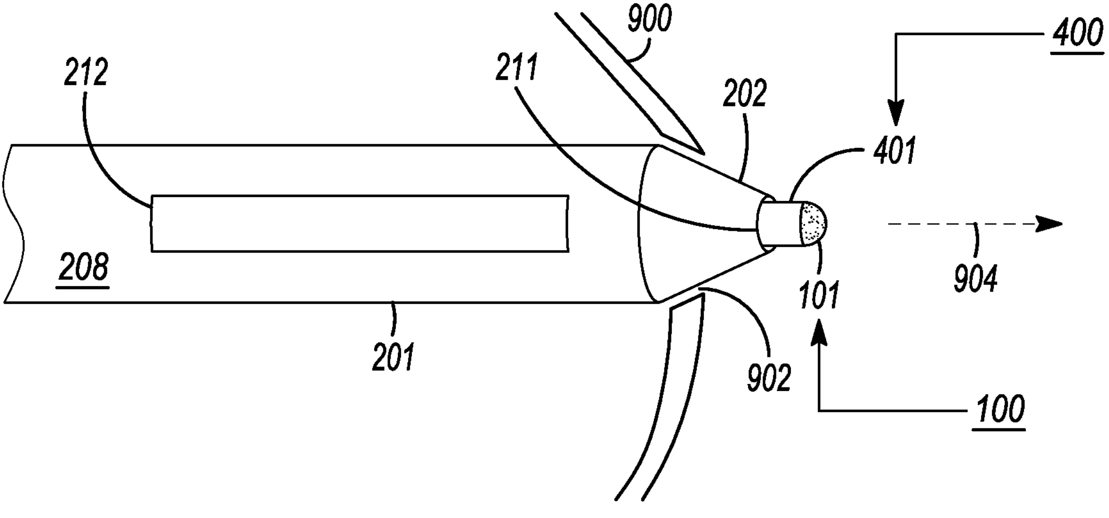

Referring to the embodiments as depicted in FIG. 9 and FIG. 10, the method further includes the step of providing energy (such as, radio-frequency energy) to the first energy-emitting device 101 (after the biological feature 900 is tented), so that the first energy-emitting device 101 initially forms the puncture hole 902 extending through the biological feature 900.

Referring to the embodiment as depicted in FIG. 10, the method further includes the step of confirming access to the biological feature 900 (such as left atrium access, etc.).

Figure 11:
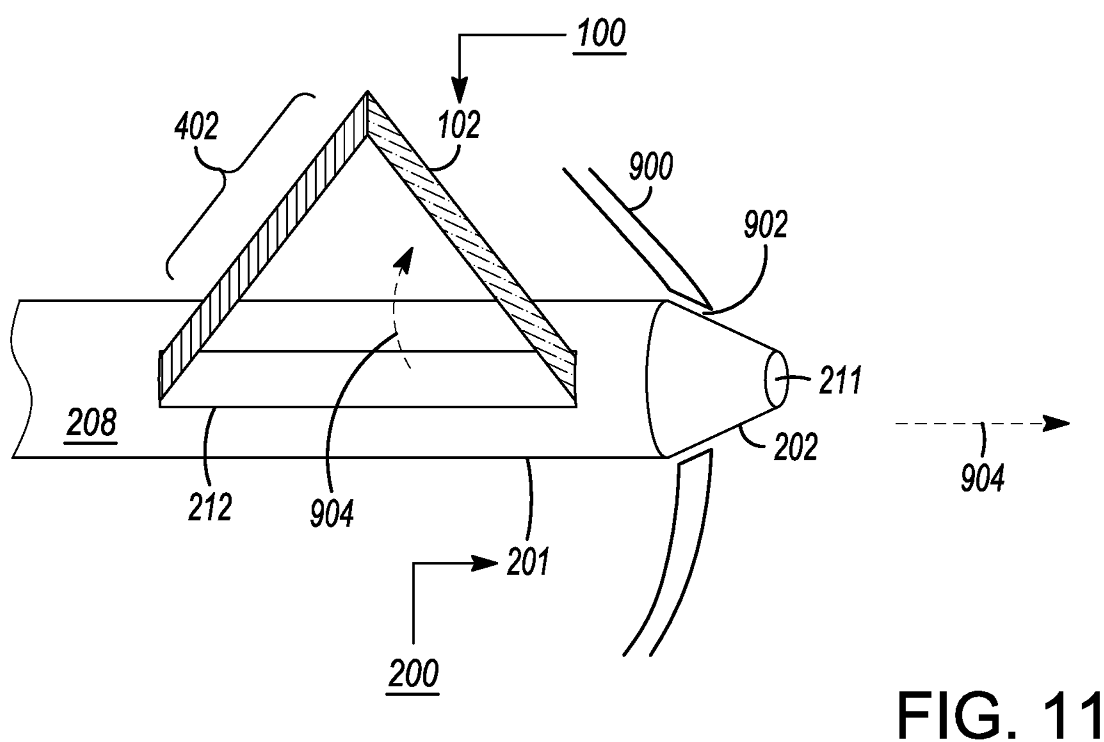

Referring to the embodiment as depicted in FIG. 11, the method further includes the step of deploying the second energy-emitting device 102 (extending or pivoting the second energy-emitting device 102 from an interior of the elongated medical assembly 200 to an exterior of the elongated medical assembly 200 via the second portal 212). Preferably, the second energy-emitting device 102 is positioned (once deployed) closer to the puncture hole 902. A section of the elongated medical needle 400 selectively forms a lever formation that extends through the second portal 212 to form a deployment shape (such as a triangle, etc.).

Figure 12:
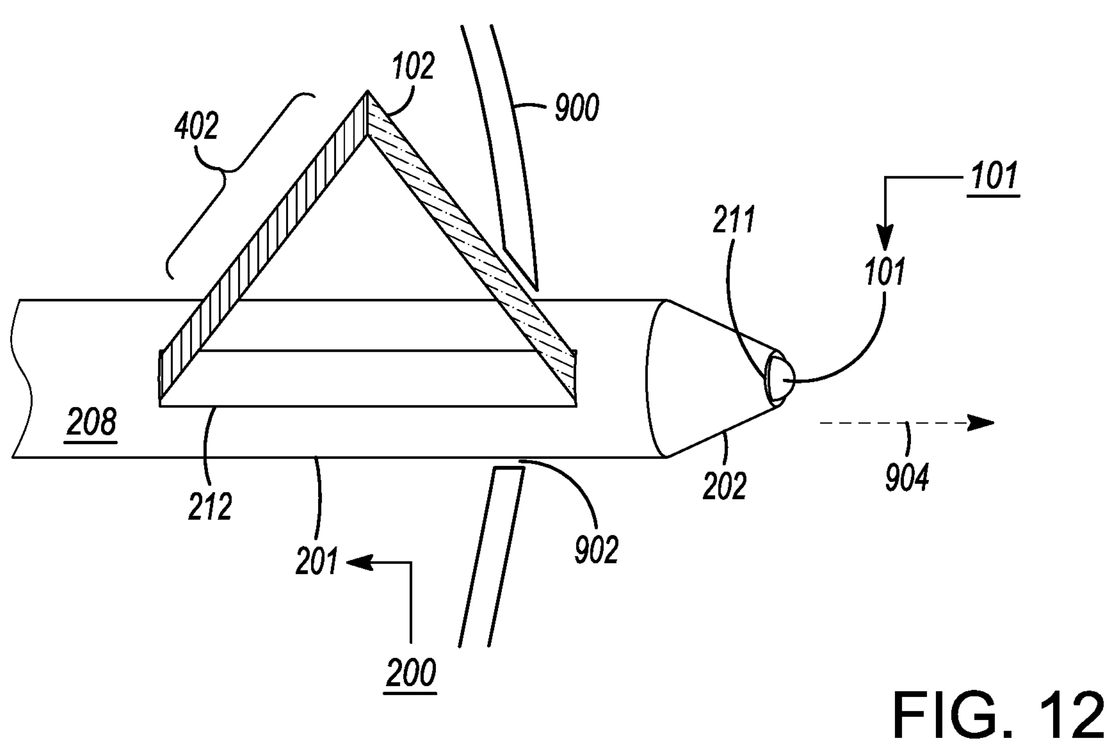

Referring to the embodiment as depicted in FIG. 12, the method further includes the step of applying energy to the second energy-emitting device 102 and advancing the second energy-emitting device 102 toward the puncture hole 902 (toward the tissue neighboring the puncture hole 902); this is done in such a way that the second energy-emitting device 102 may cross the biological feature 900 (the inter-atrial septum). The method further includes the step of continuing with any remaining aspects of the procedure (e.g. cryoablation, mitral valve repair and left atrial appendage closure, etc.).

Referring to the embodiments as depicted in FIG. 10 and FIG. 12, the first energy-emitting device 101 is configured to puncture, and form, the puncture hole 902 through the biological feature 900 (such as a biological wall, tissue, etc.) of the patient (such as, the inter-atrial septum, etc.) while the first energy-emitting device 101 is moved out from the first portal 211 of the elongated medical assembly 200. The second energy-emitting device 102 is configured to further enlarge the puncture hole 902 (after the puncture hole 902 was initially formed by the first energy-emitting device 101) while the second energy-emitting device 102 is moved out from the second portal 212 of the elongated medical assembly 200 and while the elongated medical assembly 200 is further moved toward the puncture hole (so that the second energy-emitting device 102 may be moved toward the puncture hole).

Referring to the embodiments as depicted in FIG. 10 and FIG. 12, at least one energy-emitting device 101 is configured to selectively initially emit and direct energy for the initial formation of a puncture hole 902 through a biological feature 900. At least one other energy-emitting device 102 is configured to further selectively emit and direct energy for subsequent or further enlargement of the puncture hole 902 after initial formation of the puncture hole 902 by said at least one energy-emitting device (such as the energy-emitting device 101). Preferably, at least one energy-emitting device 101 and at least one other energy-emitting device 102 are configured to be mounted proximate to a distal portion of the elongated medical needle 400. At least one energy-emitting device 101, at least one other energy-emitting device 102 and the elongated medical needle 400 are configured to be deployed along (an interior of) the elongated medical assembly 200.

Referring to the embodiments as depicted in FIG. 10 and FIG. 12, a method is depicted for formation of the puncture hole 902 through the biological feature 900 by at least one energy-emitting device 101 and at least one other energy-emitting device 102 configured to be mounted proximate to the distal needle tip section 401 of the elongated medical needle 400. The elongated medical needle 400 is configured to be deployed along an elongated medical assembly 200. The method includes moving the distal tip section 202 of the elongated medical assembly 200 to the biological feature 900. The method also includes moving at least one energy-emitting device 101 and at least one other energy-emitting device 102 by moving the distal needle tip section 401 of the elongated medical needle 400 along the elongated medical assembly 200 to the biological feature 900. The method also includes selectively initially emitting and directing energy, via at least one energy-emitting device 101, for the initial formation of the puncture hole 902 through the biological feature 900. The method also includes further selectively emitting and directing energy, via at least one other energy-emitting device 102, for subsequent or further enlargement of the puncture hole 902 after initial formation of the puncture hole 902 by said at least one energy-emitting device 101.

Referring to the embodiments as depicted in FIG. 10 and FIG. 12, the elongated medical assembly 200 includes a distal tip section 202 configured to be positioned proximate to the biological feature 900. The first energy-emitting device 101 (such as a radio-frequency energy emitter) is movable toward the distal tip section 202. The first energy-emitting device 101 is configured to selectively initially emit and direct energy for the initial formation of a puncture hole 902 through the biological feature 900 (such as, the inter-atrial septum) after the first energy-emitting device 101, in use, is moved proximate to the biological feature 900. The second energy-emitting device 102 (such as a radio-frequency energy emitter) is movable toward the distal tip section 202. The second energy-emitting device 102 is configured to further emit and direct energy for subsequent or further enlargement of the puncture hole 902 (after the first energy-emitting device 101, in use, initially forms the puncture hole 902, and the second energy-emitting device 102, in use, is moved proximate to the puncture hole 902).

Referring to the embodiments as depicted in FIG. 10 and FIG. 12, the first energy-emitting device 101 is movable toward the distal tip section 202 of the elongated medical assembly 200. The first energy-emitting device 101 is configured to selectively initially emit and direct energy for the initial formation of a puncture hole 902 through the biological feature 900 (such as, the inter-atrial septum) after the first energy-emitting device 101, in use, is moved proximate to the biological feature 900. The second energy-emitting device 102 is movable toward the distal tip section 202. The second energy-emitting device 102 is configured to further emit and direct energy for subsequent or further enlargement of the puncture hole 902 (after the first energy-emitting device 101, in use, initially forms the puncture hole 902, and the second energy-emitting device 102, in use, is moved proximate to the puncture hole 902).

Referring to the embodiments as depicted in FIG. 10 and FIG. 12, the energy-emitting assembly 100 is movable along the elongated medical assembly 200 toward a position proximate to the biological feature 900. The energy-emitting assembly 100 is configured to direct, at least in part, the initial emission of energy toward, at least in part, the biological feature 900 for the initial formation of the puncture hole 902 extending through the biological feature 900 (after the energy-emitting assembly 100, in use, is moved along the elongated medical assembly 200 and is positioned proximate to the biological feature 900). The energy-emitting assembly 100 is also configured to further direct, at least in part, subsequent emission of energy toward, at least in part, the biological feature 900 neighboring (surrounding) the puncture hole 902 for subsequent or further enlargement of the puncture hole 902 (after the energy-emitting assembly 100 is further moved along the elongated medical assembly 200 toward the biological feature 900 neighboring (surrounding) the puncture hole 902).

Referring to the embodiments as depicted in FIG. 10 and FIG. 12, the energy-emitting assembly 100 is movable along the elongated medical assembly 200 toward a position proximate to the biological feature 900. The energy-emitting assembly 100 is configured to direct, at least in part, the initial emission of energy toward, at least in part, the biological feature 900 for the initial formation of the puncture hole 902, extending through the biological feature 900 (after the energy-emitting assembly 100, in use, is moved along the elongated medical assembly 200 and is positioned proximate to the biological feature 900). The energy-emitting assembly 100 is also configured to further direct, at least in part, subsequent emission of energy toward, at least in part, the biological feature 900 neighboring (surrounding) the puncture hole 902 for subsequent or further enlargement of the puncture hole 902 (after the energy-emitting assembly 100 is further moved along the elongated medical assembly 200 toward the biological feature 900 neighboring (surrounding) the puncture hole 902).

Referring to the embodiments as depicted in FIG. 10 and FIG. 12, the energy-emitting assembly 100 is movable along the elongated medical assembly 200 toward a position proximate to the biological feature 900. The energy-emitting assembly 100 is configured to direct, at least in part, the initial emission of energy toward, at least in part, the biological feature 900 for the initial formation of the puncture hole 902, extending through the biological feature 900 (after the energy-emitting assembly 100, in use, is moved along the elongated medical assembly 200 and is positioned proximate to the biological feature 900). The energy-emitting assembly 100 is also configured to further direct, at least in part, subsequent emission of energy toward, at least in part, the biological feature 900 neighboring (surrounding) the puncture hole 902 for subsequent or further enlargement of the puncture hole 902 after the energy-emitting assembly 100 is further moved along the elongated medical assembly 200 toward the biological feature 900 neighboring (surrounding) the puncture hole 902. Preferably, the energy-emitting assembly 100 includes a first energy-emitting device 101 movable along the elongated medical assembly 200. The first energy-emitting device 101 is configured to selectively direct, at least in part, the initial emission of energy toward, at least in part, the biological feature 900 for the initial formation of the puncture hole 902 through the biological feature 900 after the distal tip section 202 and the first energy-emitting device 101, in use, are positioned proximate to the biological feature 900. Preferably, the energy-emitting assembly 100 also includes a second energy-emitting device 102 movable along the elongated medical assembly 200. The second energy-emitting device 102 is configured to selectively direct, at least in part, subsequent emission of energy toward the biological feature 900 neighboring (surrounding) the puncture hole 902 for further or subsequent enlargement of the puncture hole 902 after the second energy-emitting device 102, in use, is further moved toward the biological feature 900 neighboring (surrounding) the puncture hole 902.

Referring to the embodiments as depicted in FIG. 10 and FIG. 12, a method is provided for operating the elongated medical assembly 200 including a distal tip section 202 configured to be moved and positioned proximate to a biological feature 900. An energy-emitting assembly 100 is configured to be moved and positioned proximate to the distal tip section 202. The method includes moving and positioning the distal tip section 202 of the elongated medical assembly 200 proximate to the biological feature 900. The method also includes moving and positioning the energy-emitting assembly 100 proximate to the distal tip section 202 after the distal tip section 202 is moved and positioned proximate to the biological feature 900. The method also includes activating the energy-emitting assembly 100, after the distal tip section 202 is moved and positioned proximate to the biological feature 900, and the energy-emitting assembly 100 is moved and positioned proximate to the distal tip section 202, in such a way that the energy-emitting assembly 100, once activated, directs, at least in part, the emission of energy toward, at least in part, the biological feature 900, with the emission of energy forming a puncture hole 902 extending through the biological feature 900. The method also includes moving the distal tip section 202 further (more so) toward the puncture hole 902 formed through the biological feature 900 after the puncture hole 902 is formed and extends through the biological feature 900. The method also includes activating the energy-emitting assembly 100, after the distal tip section 202 is further moved toward the puncture hole 902, in such a way that the energy-emitting assembly 100, once activated, directs, at least in part, further emission of energy toward, at least in part, the biological feature 900 surrounding, and positioned proximate to, the puncture hole 902, with the further emission of energy further enlarging the puncture hole 902 as (while) the distal tip section 202 moves further (more so) toward the puncture hole 902. The method may also include activating a first energy-emitting device 101 of the energy-emitting assembly 100 to form the puncture hole 902 through the biological feature 900 after the distal tip section 202 and the first energy-emitting device 101, in use, are placed proximate to the biological feature 900, and the first energy-emitting device 101, in use, is activated to direct, at least in part, the emission of energy toward, at least in part, the biological feature 900 for forming the puncture hole 902. The method may also include activating a second energy-emitting device 102 of the energy-emitting assembly 100 to further enlarge the puncture hole 902 after the puncture hole 902 is formed by the first energy-emitting device 101, and the second energy-emitting device 102 is activated to direct, at least in part, further emission of energy toward the biological feature 900 surrounding, and positioned proximate to, the puncture hole 902 for further enlargement of the puncture hole 902.

Referring to the embodiments as depicted in FIG. 10 and FIG. 12, an apparatus is provided for formation of the puncture hole 902 to be extended through the biological feature 900. The apparatus is for use with an elongated medical assembly 200 including a distal tip section 202 configured to be moved and positioned proximate to the biological feature 900. The apparatus includes an energy-emitting assembly 100 movable along the elongated medical assembly 200, and positionable proximate to the distal tip section 202. The energy-emitting assembly 100 is configured to direct, at least in part, the initial emission of energy toward, at least in part, the biological feature 900 for the initial formation of the puncture hole 902 through the biological feature 900 after the distal tip section 202 and the energy-emitting assembly 100, in use, are moved and positioned proximate to the biological feature 900. The energy-emitting assembly 100 is also configured to further direct, at least in part, further emission of energy from the energy-emitting assembly 100 toward, at least in part, the biological feature 900 neighboring (surrounding) the puncture hole 902 for further enlargement of the puncture hole 902 after the distal tip section 202 and the energy-emitting assembly 100, in use, are moved further (more so) toward (closer) to the puncture hole 902.

Referring to the embodiments as depicted in FIG. 10 and FIG. 12, an apparatus is for formation of the puncture hole 902 to be extended through the biological feature 900. The apparatus is for use with an elongated medical assembly 200 including a distal tip section 202 movable and positionable proximate to the biological feature 900. The apparatus includes an energy-emitting assembly 100 movable along the elongated medical assembly 200, and positionable proximate to the distal tip section 202. The energy-emitting assembly 100 is configured to be activated after the distal tip section 202 is moved and positioned proximate to the biological feature 900. The energy-emitting assembly 100 is moved and positioned proximate to the distal tip section 202 in such a way that the energy-emitting assembly 100, once activated, directs, at least in part, the emission of energy toward, at least in part, the biological feature 900, with the emission of energy forming the puncture hole 902 extending through the biological feature 900. The energy-emitting assembly 100 is also configured to be activated after the distal tip section 202 is further moved toward the puncture hole 902 in such a way that the energy-emitting assembly 100, once activated, directs, at least in part, further emission of energy toward, at least in part, the biological feature 900 surrounding, and positioned proximate to, the puncture hole 902, with the further emission of energy further enlarging the puncture hole 902 as (while) the distal tip section 202 moves further (more so) toward the puncture hole 902.

Figure 13:
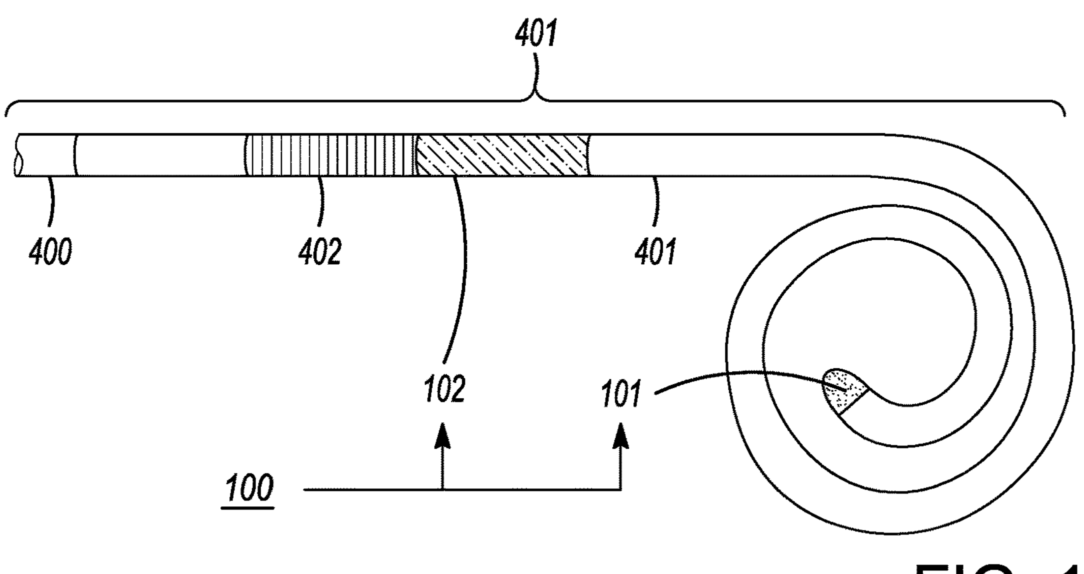
FIG. 13 to FIG. 15 depict side views (FIG. 13 and FIG. 14) and a side perspective view (FIG. 15) of embodiments of the energy-emitting assembly of FIG. 1.
Figure 14:
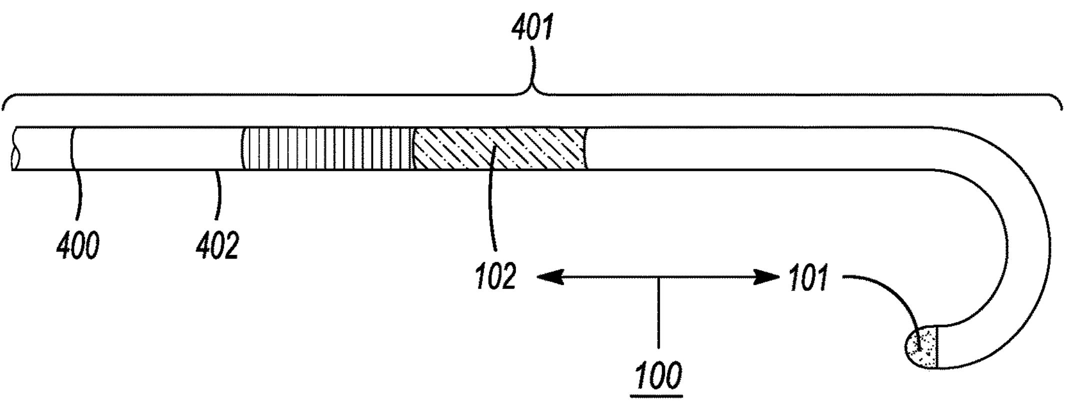
Figure 15:
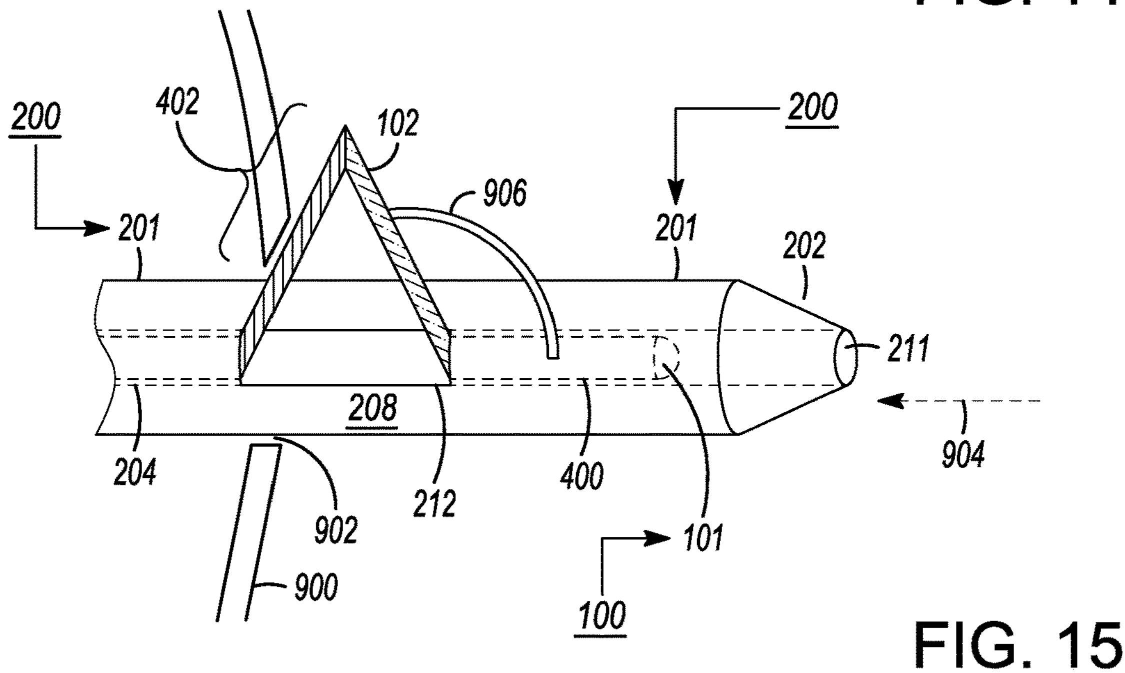

FIG. 13 to FIG. 15 depict side views (FIG. 13 and FIG. 14) and a side perspective view (FIG. 15) of embodiments of the energy-emitting assembly 100 of FIG. 1.

Referring to the embodiments as depicted in FIG. 13 and FIG. 14, the elongated medical needle 400 may include any type of tips, such as a J-tip (as depicted in FIG. 14) or a pigtail (as depicted in FIG. 13), so as to secure access after puncturing and enlarging the septum, etc.

Referring to the embodiment as depicted in FIG. 15, the surgeon may pull (along the movement direction 904), rather than push, the elongated medical needle 400 to enlarge the puncture hole 902. In this configuration, the formation of the section of the elongated medical needle 400 (that pivots outwardly from an interior of the elongated medical assembly 200) may be located between the first energy-emitting device 101 and the second energy-emitting device 102. It will be appreciated that a mechanism (not depicted) may be provided for the surgeon to decide how large to make the puncture hole 902 (e.g. a small hole versus a large hole). A distal angle 906 is formed between the elongated medical needle 400 (the radiofrequency wire) and the elongated medical assembly 200 when (once or after) the second energy-emitting device 102 is deployed from the interior of the elongated medical assembly 200. The size of the distal angle 906 may be optimized to facilitate cutting of tissue by utilization of (emission of) energy from the second energy-emitting device 102, such as radiofrequency energy, etc. The size of the distal angle 906 may be (preferably) greater than 90 degrees.

FIG. 16 to FIG. 19 depict side views of embodiments of the energy-emitting assembly 100 of FIG. 1.

Referring to the embodiment as depicted in FIG. 16, the first energy-emitting device 101 and the second energy-emitting device 102 are coaxially aligned with each other. The first energy-emitting device 101 and the second energy-emitting device 102 remain coaxially aligned with each other once, or when, they are activated as in FIG. 18 or FIG. 19, or while they remain inactivated as in FIG. 17. The front ends of the first energy-emitting device 101 and the second energy-emitting device 102 provide (preferably) a slopped frontal surface (blunt surface) for smoother formation of a puncture hole, and subsequent enlargement thereof.

Referring to the embodiment as depicted in FIG. 16, it will be appreciated that the outer diameter of the elongated medical needle 400 may be the same diameter on both sides of the second energy-emitting device 102 (if desired).

Referring to the embodiment as depicted in FIG. 17, the first energy-emitting device 101 and the second energy-emitting device 102 are inactivated as in FIG. 17 while the distal tip portion of the elongated medical needle 400 is moved toward the biological feature 900 (along the movement direction 904).

Referring to the embodiment as depicted in FIG. 18, the second energy-emitting device 102 is deactivated, and the first energy-emitting device 101 is activated to initially form (create) the puncture hole 902 through the biological feature 900 (while the elongated medical needle 400 is moved along the movement direction 904 so that the first energy-emitting device 101 contacts the surface of the biological feature 900).

Referring to the embodiment as depicted in FIG. 19, the first energy-emitting device 101 is deactivated (after formation of the puncture hole 902), and the second energy-emitting device 102 is further moved toward the puncture hole 902 (the neighboring tissue surrounding the puncture hole 902), and the second energy-emitting device 102 is activated for subsequent enlargement of the puncture hole 902 through the biological feature 900 (after the puncture hole 902 was formed by the first energy-emitting device 101, as depicted in FIG. 18, and while the elongated medical needle 400 is moved along the movement direction 904 and through the puncture hole 902).

Referring to the embodiments as depicted in FIG. 18 and FIG. 19, at least one energy-emitting device 101 is configured to selectively initially emit and direct energy for the initial formation of a puncture hole 902 through a biological feature 900. At least one other energy-emitting device 102 is configured to further emit and direct energy for subsequent further enlargement of the puncture hole 902 after initial formation of the puncture hole 902 by said at least one energy-emitting device 101.

Referring to the embodiments as depicted in FIG. 18 and FIG. 19, the energy-emitting assembly 100 is (preferably) mounted to the elongated medical needle 400. The first energy-emitting device 101 is mounted, at least in part, to a distal tip section of the elongated medical needle 400. The second energy-emitting device 102 is mounted to, at least in part, a circumference of the elongated medical needle 400. The first wire 411 extends, at least in part, along the elongated medical needle 400. The first wire 411 is electrically connected to the first energy-emitting device 101. The second wire 412 extends, at least in part, along the elongated medical needle 400. The second wire 412 is electrically connected to the second energy-emitting device 102. The first wire 411 and the second wire 412 are configured to be electrically connected to at least one or more energy sources 500. The first energy-emitting device 101 and the second energy-emitting device 102 (preferably) are movable from an interior of the elongated medical assembly 200 via the first portal 211 of the elongated medical assembly 200.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for formation of a puncture hole to be extended through a biological feature, and for use with an elongated medical assembly, and the apparatus comprising:

an energy-emitting assembly movable along the elongated medical assembly toward a position proximate to the biological feature; and the energy-emitting assembly including a first energy-emitting device configured to direct, at least in part, initial emission of energy toward, at least in part, the biological feature for initial formation of the puncture hole, extending through the biological feature, after the energy-emitting assembly, in use, is moved along the elongated medical assembly and is positioned proximate to the biological feature; and the energy-emitting assembly including a second energy-emitting device configured to further direct, at least in part, subsequent emission of energy toward, at least in part, the biological feature neighboring the puncture hole for subsequent enlargement of the puncture hole after the energy-emitting assembly is further moved along the elongated medical assembly toward the biological feature neighboring the puncture hole;

wherein, the elongated medical assembly includes a lumen configured to receive the energy-emitting assembly, a first distal portal, and a second proximal portal that is spaced from the first distal portal; and wherein, the second energy-emitting device is configured to extend from the second proximal portal while the first energy-emitting device is located in the lumen.

2. The apparatus of claim 1, wherein:

the first energy-emitting device movable along the elongated medical assembly; and the first energy-emitting device configured to selectively direct, at least in part, initial emission of energy toward, at least in part, the biological feature for initial formation of the puncture hole through the biological feature after the first energy-emitting device, in use, is positioned proximate to the biological feature; and the second energy-emitting device movable along the elongated medical assembly; and the second energy-emitting device configured to selectively direct, at least in part, subsequent emission of energy toward the biological feature neighboring the puncture hole for further subsequent enlargement of the puncture hole after the second energy-emitting device, in use, is further moved toward the biological feature neighboring the puncture hole.

3. The apparatus of claim 2, wherein:

the energy-emitting assembly is mounted to an elongated medical needle; and the first energy-emitting device is mounted, at least in part, to a distal tip section of the elongated medical needle; and the second energy-emitting device is mounted to, at least in part, a circumference of the elongated medical needle; and a first wire extends, at least in part, along the elongated medical needle, and the first wire is electrically connected to the first energy-emitting device; and a second wire extends, at least in part, along the elongated medical needle, and the second wire is electrically connected to the second energy-emitting device; and the first wire and the second wire are configured to be electrically connected to an energy source.

4. The apparatus of claim 3, wherein:

the second energy-emitting device is configured to be mounted to the elongated medical needle; and the elongated medical needle is configured to selectively move the second energy-emitting device from within an interior of the elongated medical assembly to an exterior of the elongated medical assembly via a second portal of the elongated medical assembly.

5. The apparatus of claim 4, wherein:

the elongated medical assembly includes the distal tip section, and the distal tip section forms the first distal portal.

6. The apparatus of claim 4, wherein:

the elongated medical assembly includes a side wall section, and the side wall section forms the second portal.

7. The apparatus of claim 4, wherein:

the elongated medical needle is configured to be selectively moved so that the first energy-emitting device is moved from within the elongated medical assembly to externally of the elongated medical assembly via the first distal portal.

8. The apparatus of claim 7, wherein:

the elongated medical needle is configured to be selectively shaped to move the second energy-emitting device from within the elongated medical assembly to externally of the elongated medical assembly via the second portal.

9. The apparatus of claim 8, wherein:

the second energy-emitting device is configured to be moved from within the elongated medical assembly and positioned outside of the elongated medical assembly.

10. The apparatus of claim 3, wherein:

the elongated medical needle includes a shape-memory material.

11. The apparatus of claim 1, wherein:

the elongated medical assembly includes a catheter assembly.

12. The apparatus of claim 1, wherein:

the first energy-emitting device and the second energy-emitting device are movable from an interior of the elongated medical assembly via a first portal of the elongated medical assembly.

13. An apparatus for formation of a puncture hole to be extended through a biological feature, and for use with an elongated medical assembly, and the apparatus comprising:

an energy-emitting assembly movable along the elongated medical assembly toward a position proximate to the biological feature; and the energy-emitting assembly configured to direct, at least in part, initial emission of energy toward, at least in part, the biological feature for initial formation of the puncture hole, extending through the biological feature, after the energy-emitting assembly, in use, is moved along the elongated medical assembly and is positioned proximate to the biological feature; and the energy-emitting assembly also configured to further direct, at least in part, subsequent emission of energy toward, at least in part, the biological feature neighboring the puncture hole for subsequent enlargement of the puncture hole after the energy-emitting assembly is further moved along the elongated medical assembly toward the biological feature neighboring the puncture hole;

wherein, the energy-emitting assembly includes:

a first energy-emitting device movable along the elongated medical assembly; and a second energy-emitting device movable along the elongated medical assembly; and wherein, the elongated medical assembly forms a first portal and a second portal that are spaced apart from each other; and the first portal is configured to interact with the first energy-emitting device; and the first energy-emitting device is configured to pass through, at least in part, the first portal.

14. The apparatus of claim 13, wherein:

the second portal is configured to interact with the second energy-emitting device; and the second energy-emitting device is configured to pass through, at least in part, the second portal.

* * * * *